United States Patent [19]
Nakamura et al.

[11] Patent Number: 5,826,983
[45] Date of Patent: Oct. 27, 1998

[54] THERMOMECHANICAL ANALYZER EQUIPPED WITH A THERMOGRAVIMETRY FUNCTION

[75] Inventors: Nobutaka Nakamura; Yoshiharu Sugano, both of Chiba, Japan

[73] Assignee: Seiko Instruments Inc., Chiba, Japan

[21] Appl. No.: 678,045

[22] Filed: Jul. 10, 1996

[30] Foreign Application Priority Data

Jul. 11, 1995 [JP] Japan ................................. 7-175095

[51] Int. Cl.⁶ .......................... G01N 25/00; G01N 25/16
[52] U.S. Cl. ................... 374/14; 374/55; 374/56
[58] Field of Search .................. 374/14, 55, 56

[56] References Cited

U.S. PATENT DOCUMENTS

| | | | |
|---|---|---|---|
| 3,271,996 | 9/1966 | Paulik et al. | 374/14 |
| 3,554,001 | 1/1971 | Norem | 374/14 |
| 4,896,973 | 1/1990 | Hill et al. | 374/56 |
| 4,976,549 | 12/1990 | Khan | 374/55 |
| 5,466,066 | 11/1995 | Hidaka | 374/14 |

FOREIGN PATENT DOCUMENTS

| | | | |
|---|---|---|---|
| 0181643 | 9/1985 | Japan | 374/55 |
| 402227647 | 9/1990 | Japan | 374/55 |
| 404256830 | 9/1992 | Japan | 374/14 |
| 404299234 | 10/1992 | Japan | 374/55 |
| 2068123 | 8/1981 | United Kingdom | 374/56 |

*Primary Examiner*—Diego F. F. Gutierrez
*Attorney, Agent, or Firm*—Loeb & Loeb LLP

[57] ABSTRACT

A thermomechanical analyzer capable of performing, in addition to thermomechanical measurement, thermogravimetry of a sample of several grams or more only by switching parts of the analyzer. A thermomechanical analyzer has a heating furnace, a temperature detector for detecting temperature of the sample that is placed within the heating furnace, an attachable/detachable detecting rod and a sample holding member, wherein the sample is held between the detecting rod and the sample holding member. A load applying instrument applies an external force to the sample via the detecting rod. A displacement detector detects displacement of the detecting rod relative to the sample holding member. The thermomechanical analyzer is provided with a control computing apparatus for adjusting an output from the load applying instrument to bring an output from the displacement detector closer to a fixed value. The detecting rod and the sample holding member in the thermomechanical analyzer may be replaced respectively with a sample container and a container holding member. A recording device records output from the temperature detector and the load applying instrument.

10 Claims, 5 Drawing Sheets

THERMOMECHANICAL ANALYZER EQUIPPED WITH A THERMOGRAVIMETRY FUNCTION

BACKGROUND OF THE INVENTION

The present invention relates to a thermal analyzer for investigating the dependence of a characteristic or property of a material on temperature. More particularly, the invention relates to a novel improved device which functions as a thermogravimetry analizer for measuring the weight of a sample as a temperature or time function or as a thermomechanical analyzer for measuring a physical characteristic of a sample as a temperature or time function.

Thermal analysis is an effective means for investigating how a physical or chemical characteristic of a material changes depending on temperatures changes. Thermal analysis is a generic term for measuring techniques for measuring dependence of a property on temperature. Representative thermal analyzers include differential, scanning calorimeters (DSC), deviation, or differential thermal analyzers (DTA), thermogravimetric analyzers (TG) and thermomechanical analyzers (TMA). These are designed respectively to measure an enthalpy balance, differential heat (qualitative enthalpy balance), the weight, and a dimension of a sample as a function of temperature. These thermal analyzers provide complementary pieces of information on a sample in many cases. Thus, those engaged in measurement may often wish to employ as many kinds of thermal analyzers as possible such that they can carry out multifaceted analysis of a sample. In order to satisfy such a demand from those engaged in measurement, device manufacturers have provided to the market products like the following:

(1) Thermal analysis systems for controlling a plurality of thermal analyzers, in which unnecessary parts have been omitted and the functions of controlling temperature and recording and analyzing measurement data have been integrated; and (2) Simultaneous measuring devices formed by incorporating the functions of a differential scanning calorimeter (hereinafter, the device and its measuring method are called DSC together) and a differential thermal analyzer (hereinafter, the device and its measuring method are called DTA together) in another thermal analyzer, for instance a thermogravimetric device (hereinafter, the device and its measuring method are called TG together).

A thermomechanical measuring device (hereinafter, the device and its measuring method are called TMA together) has been utilized for measuring the thermal expansion coefficient and softening temperature of a sample from a change in a dimension of the sample when the temperature of the sample is changed under a fixed load applied by a pressing rod. In addition, this has often been used for measuring such mechanical characteristics as tension, bending and the like by changing the tip form of a detecting rod. Further, the present inventors have presented TMA equipped with a function for program-controlling a load or displacement, which allows measuring of static as well as dynamic viscoelasticity of a sample in addition to its dimension (Netdusokutei no Shinpo Vol. 5, page 79 to 86, issued by Science and Technology, Inc., in 1987, Tokyo, Japan). This TMA has already been placed on the market.

There are available two types of TG, a microtype TG targeting for its measurement samples of several hundred milligrams or less so as to minimize the temperature distribution within a sample by making the sample quantity minute, and a macrotype TG targeting for its measurement samples of several grams or more so as to minimize the effect of composition distribution within a sample. In both of these types, a sample is heated and cooled according to a predetermined temperature program and a change in the weight of the sample is measured as a function of temperature or time.

In the above-described prior art, there has been presented no report on a thermal analyzer capable of performing measurement of both TMA and TG with one device. Also, since requirements for the device are different between the microtype TG and the macrotype TG with respect to the size of a sample container and maximum and minimum values of weight measurement, it has been impossible to integrate these in one device. As a result, when TG and TMA are to be utilized for evaluating a given material according to the prior art, at least two thermal analyzers or even three in some cases must be needed, creating problems of space and cost, and a waste of resources.

SUMMARY OF THE INVENTION

In order to provide improved testing capabilities, the present invention provides a thermal analyzer for carrying out thermomechanical analysis and thermogravimetry. This thermal analyzer includes a heating furnace for heating a sample according to a prescribed temperature program, a temperature detector disposed proximate to the sample for detecting a temperature of the sample, sample supporting means for supporting the sample on one end thereof, a displacement detector disposed in a portion of the sample supporting means for detecting displacement of the sample supporting means, a load applying instrument for applying an external force to the sample via the sample supporting means, a control computing element for supplying to the load applying instrument a signal for controlling the external force applied from the load applying instrument to the sample so as to make the displacement of the sample supporting means zero based on an output from the displacement detector, a switch included in the control computing element for switching the control computing element to output to the load applying instrument a signal for controlling the external force applied from the load applying instrument to the sample to a predetermined value and a storage instrument for storing as thermogravimetry data, values derived from the signal supplied from the control computing element for controlling the external force applied from the load applying instrument to the sample so as to set the displacement of the sample supporting means to zero when the switch does not perform switching and storing as thermomechanical analysis data, values derived from a signal supplied from the displacement detector.

Now, the action of the thermal analyzer configured in the above-stated manner for both TMA and TG measurement will be described.

In the case of TMA measurement, first the temperature of a sample is changed according to a prescribed program by changing the temperature in the heating furnace while applying a fixed load (or a load which varies according to a specified time function) from the load supplying instrument to the sample via the sample holding member detecting rod from the upper end of the sample. During this operation, the sample temperature and a change in its dimension are captured respectively by the temperature detector and the displacement detector. The results thereof are stored, thereby completing the TMA measurement (a temperature function of the sample dimension or a time function thereof has been obtained).

In the case of TG measurement, a sample container is suspended so as to float in the tip of the sample holding member. Then, the control computing element is actuated and the control computing element adjusts an output from the load applying instrument such that the output from the displacement detector may be set to a fixed value, for instance zero. During this operation, the output from the load applying instrument is balanced with a tare weight, or empty container weight, and this tare weight value is eliminated by resetting only the recorded value of the output from the load applying instrument to zero while keeping the current output thereof intact. The sample is placed into a container while continuing the operation of the control computing element and by changing the temperature of the heating furnace, the temperature of the sample is changed at a fixed rate (or a prescribed program rate). At this time, the sample temperature is captured by the temperature detector. The weight of the sample is based on the output value from the load applying instrument and the result thereof is stored, thereby completing the TG measurement (a temperature function of the sample weight or a time function of the sample dimension has been obtained).

These two cases show that it is possible to achieve the object of carrying out TMA measurement and TG measurement by using one device.

DESCRIPTION OF THE PREFERRED EMBODIMENTS

Next, preferred embodiments of the invention will be described in detail for both cases, TG measurement and TMA measurement.

Figure 1:
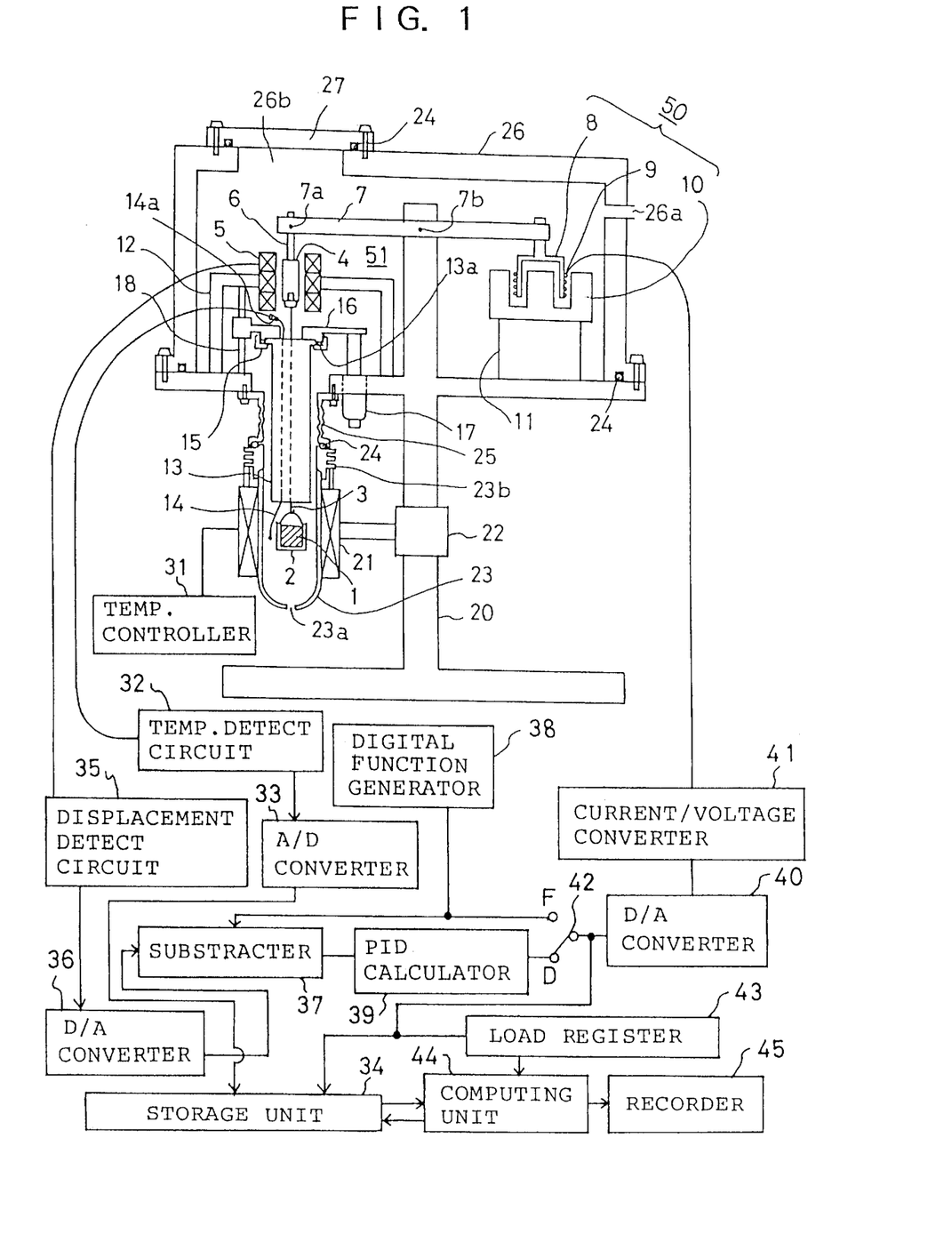
FIG. 1 is partly a simplified pictorial view and partly a block diagram of a system for thermogravimetry (TG) according to a first embodiment of the invention.

FIG. 1 is a sectional view showing the application of the analyzer of the invention to TG measurement. In FIG. 1, a sample 1 is housed in a sample container 2 made of platinum. The sample container 2 is placed in a heating furnace 21 for heating the sample and the heating furnace 21 is heated by means of a temperature program programmed by a temperature controller 31. This can also be cooled in cooling step programmed by a cooling means, not shown. The sample container 2 is suspended by a suspension wire 3 made of a thermally stable material, for instance platinum, and fixed by a screw to a core 4 by the upper tip of the suspension wire 3. The core 4 constitutes the displacement detector together with a differential transformer 5 placed surrounding the core 4 and detects displacement of the suspension wire 3 in its up and down directions. A detecting rod 6 is fixed to the upper end of the core 4. The sample container 2, the suspension wire 3, the core 4 and the detecting rod 6 are placed in a linear form (vertically). A connecting rod 6 is connected to the subfulcrum 7a of an arm 7 so as to be freely rotated and attached or detached when necessary. The arm 7 is supported on a structuring member 20 by a main fulcrum 7b freely rotatably almost in a lateral direction, forming a kind of a balancing system. The sample container 2, the suspension wire 3, the core 4, the connecting rod 6 and the arm 7 together define a sample supporting means. In FIG. 1, the sample supporting means functions to transmit an external force from a load applying instrument 50 to the sample 1 and detects deformation and weight of the sample 1.

A coil holder 8 is fixed to an end of the arm 7 (not necessarily an end) in a side opposite to the subfulcrum 7a of the arm 7 and a coil 9 is wound on the coil holder 8. The coil 9 constitutes the load applying instrument 50 for applying an external force to the sample by means of an electromagnetic force integrally with a magnet 10 and the coil holder 8 placed around the coil 9 with a space. A force can be transmitted to the subfulcrum 7a side via the arm 7 by adjusting a current value flowing to the coil 9. This means that an external force can be applied to the sample 1 via the sample supporting means. The magnet 10 is fixed to the structuring member 20 via a base 11. The differential transformer 5 is fixed to the structuring member 20 via a holding material 12. A reference numeral 13 represents a protective tube equipped with a flange part 13a. A thermocouple 14 incorporated in a double-core tube is fixed to the inner side of the protective tube 13 and a connector 14a is provided in the end (upper part) of the thermocouple 14.

The protective tube 13 is fixed by a screw to a sample tube holder 16 by means of a fixing nut 15 in the flange part 13a. One end of the sample tube holder 16 is supported in the tip part of a micrometer 17 while the other end is supported freely movably up and down against a columnar guiding rod 18 fixed between the holding member 12 and the structuring member 20. A portion of the body of the micrometer 17 is fixed to the structuring member 20 and thus by rotating the micrometer 17, the sample holder 16, the protective tube 13 and the tip position of the thermocouple 14 fixed to the protective tube 13 can be moved up and down. The heating furnace 21 is provided for heating the sample 1 via a furnace tube 23. The heating furnace 21 is fixed to a moving mechanism 22 provided in the structuring member 20 and can move the heating furnace 21 up and down by the function of the moving mechanism 22.

An exhaust hole 23a is provided in a bottom part inside the heating furnace 21 and the furnace tube 23 having a heat radiating flange 23b is fixed to an upper part. The heat radiating flange 23b of the furnace tube 23 is in contact with a tube-formed bellows 25 via an O-ring 24 and the upper end of the tube-formed bellows 25 is fixed to the structuring member 20. The upper part of the analyzer is hermetically sealed by screwing a cover 26 to the structuring member 20. An atmosphere in the sample 1 can be changed by introducing a gas through a gas introducing port 26a provided in the cover 26. The introduced gas is discharged to the outside of the analyzer through the hole 23a of the furnace tube 23. Further, an opening part 26b is provided in the upper part of the cover 26 and by removing a cap, the connecting rod 6, the core 4 and the suspension wire 3 can be easily removed together.

The heating furnace 21 is connected to a temperature controller 31 and heats up the temperature of the sample 1 in accordance with a preset program. Also, by introducing a coolant into the furnace tube, the sample 1 can be cooled under control in specified cooling step.

The thermocouple 14 provided with the connector 14a is connected to a temperature detector 32 and passed through a first A/D converter 33 and the temperature of the sample 1 or a temperature in the vicinity thereof is sent to a storage instrument 34 as a digital signal. Generally, a temperature program used for heating and cooling the sample is linear (linear function). Instead of a temperature signal, a time signal may be stored in the storage instrument 34 in many cases.

The differential transformer 5 is placed in the outer periphery of the core 4 with a space provided. Since an output from the differential transformer 5 indicates the position of the core 4, displacement in position of the sample supporting means with the core 4 attached can be detected. This means that the core 4 and the differential transformer 5 constitute a displacement detector.

A displacement detecting circuit 35 is connected to the differential transformer 5 and a resetting operation is performed so as to make displacement zero when noises are eliminated and the core 4 is in a specified position. An output from the displacement detecting circuit 35 is sent to a second A/D converter 36 in order to convert an analog signal into a digital signal and then sent to the storage instrument 34 as a digitized displacement signal. A subtracter 37 connected to the second A/D converter 36 is also connected to a digital function generator 38. The digital function generator supplies a digital signal based on a fixed number or a sine wave function. A difference in outputs between the digital function generator and the second A/D converter is supplied to a PID computing element 39.

A D/A converter 40 is provided, to which a digital signal from the PID computing element or the digital function generator 38 is supplied via a switch 42 when the switch is turned to a D side. The D/A converter 40 in turn converts the signal into an analog signal and outputs this to a current/voltage converter 41 so as to convert it into a voltage signal. The current/voltage converter 41 is connected to the coil 9. The PID computing element 39 supplies a signal for controlling a load applying instrument 50 via the switch 42, the A/D converter 40 and the current/voltage converter 41 so as to keep to a fixed value a difference in a signal indicating the displacement of the core 4 of the differential transformer 5 constituting the displacement detector and a signal from the digital function computing element 38 when the switch 42 is turned to the D side.

The switch 42 starts inputting to the D/A converter 40 from the digital function generator 38 side when the switch 42 is switched to an F side. When the switch 42 is switched to the D side, inputting is started from the PID computing element 39 side. In other words, these can be alternately switched.

A control computing element is composed of the subtracter 37, the PID computing element 39, the digital function generator 38 and the switch 42. The control computing element functions, in short as described above, to supply a signal for controlling an output from the differential transformer 5 constituting the displacement detector into a signal based on a signal supplied from the digital function generator 38 within the control computing element. This also functions to output a signal from the digital function generator 38 without any changes.

The input terminal of the D/A converter 40 is connected not only to the storage instrument 34 but also to a load register 43. A signal input to the D/A converter 40 is thus a digital value for a load signal supplied to the load applying instrument 50 and sent to the storage instrument 34. Also, a load value at this time is registered in the load register 43 according to an instruction given by a measurer. Signals respectively indicating a temperature, displacement and a load time sequentially stored in the storage instrument are given proper signal names if the measurer so wishes and sent to a computing element 44. The computing element 44 provides a value obtained by subtracting the load value registered in the load register from the load signal value sent from the storage instrument as a new load signal value to a recording device 45 such as a plotter, a printer or the like. This is then output as thermal analysis data in the form of a graph or a table.

Next, the operation of the analyzer of the invention will be described. First, the switch 42 is set to the D side (PID computing element 39 side) without the sample placed in. The detecting rod 6, the core 4, the suspension wire 3 and the sample container 2 are set in the subfulcrum 7a of the arm 7 as shown in FIG. 1. The control system forms a displacement control loop and sets an output from the digital function generator 38 to a fixed value, for instance zero. At this time, a current flows to the coil 9 such that the balance formed by the main fulcrum 7b of the arm 7 can be placed in equilibrium and a displacement output indicative of the displacement of the core 4 supplied from the displacement detecting circuit 35 is made stable at zero. By operating the load register 43, a load value calculated from a digital signal indicative of a current value at this time supplied from the PID computing element 39 is registered in the load register 43.

Then, the sample 1 is placed into the sample container 2 and the height of the thermocouple 14 is adjusted by turning on the micrometer 17. After the heating furnace 21 has been raised by the moving mechanism 22 until the heat radiating flange 23b comes into contact with the tube-formed bellows 25 via the O-ring 24, the position of the heating furnace 21 is adjusted. Also, during this time, a current flows to the coil 9 so as to place the balance formed by the main fulcrum 7b of the arm 7 in equilibrium and a displacement output indicative of the displacement of the core 4 supplied from the displacement detecting circuit 35 is made stable at zero. An output from the PID computing element 39 is caused to indicate the weight of the sample. This output is supplied to the load register 43 and the storage instrument 34.

The temperature of the heating furnace 21 is changed by means of the temperature controller 31 in accordance with a predetermined temperature program. The temperature of the sample 1 is captured by the thermocouple 14, its weight is expressed in a value of a current flowing to the coil 9 and detected as a load value of the sample 1. If any weight change occurs in the sample 1, the core 4 moves slightly in up and down directions. The displacement detector 35 electrically detects the moving amount of the core 4. A signal supplied therefrom is converted into a digital signal by the second A/D converter 36 and subtracted by a signal from the digital function generator 38 in the subtracter 37. This signal is then input to the PID computing element 39, PID controlled and passed through the D/A converter 40 and the current/voltage converter 41. Then, the load applying instrument 50 composed of the coil holder 8, the coil 9 and the magnet 10 produces a force used for returning the core 4 to its original position. This means that a change in the weight of the sample 1 can be known by calculating the changing quantity of a signal newly provided to the load applying instrument 50.

The weight other than that of the sample, for instance the sample container 2, is registered as a wind bag weight in the storage instrument 34 and eliminated inside the computing element 44. Thus, a load value output from the recording device 45 is the weight of the sample 1.

Figure 5:
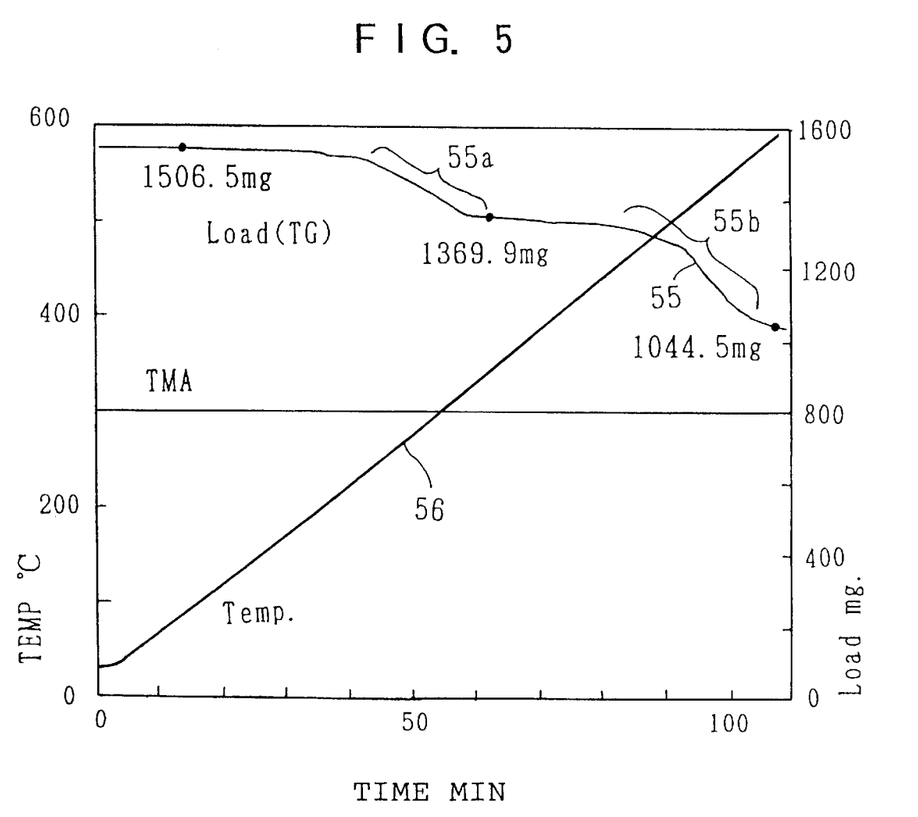
FIG. 5 is a graph showing results of TG measurement with a sample placed in a fixed position by using the analyzer shown in FIG. 1.

Data output from the PID computing element 39 as a signal for controlling the load applying instrument 50 is stored in the storage instrument 34 as a temperature function (or time function) of the weight (weight changing quantity) of the sample 1 and output to the recording device. The temperature function (or time function) of the weight (weight changing quantity) of the sample 1 is a result obtained by performing thermogravimetry. FIG. 5 shows the result of thermogravimetry. The ordinate indicates sample temperatures and weights while the abscissa indicates passages of measuring time. The thermal weight measuring result is represented by a line 55 as time function. The sample temperature is also represented by a line 56. As the sample 1, a calcium oxalate 1 hydrate of 1.54 grams in weight was used. Reaction 55a shows that the weight of the sample 1 declined due to dehydration. Reaction 55b shows that further decomposition occurred and carbon monoxide was separated. From the data, it can be understood that the weight declined by 12.8% in the reaction 55a and by 19.2% in the reaction 55b. Both show accuracy within the range of 0.5% with respect to a theoretical value.

The suspension wire 3 is long enough to place the sample 1 in a specified position with respect to the heating furnace 21. This may be in a line or a rod form as long as a thermally stable material is used. For the purpose of accuracy it is preferable to utilize a heavy material made of, for instance platinum, so as not to be floated by air. A means for freely attaching/detaching the sample container 2 is provided in an end in a side opposite to the side attached to the core 4 of the suspension wire 3. This means may be a screw, but in the embodiment this is a hook. For the sample container 2, though a bucket form with a handle is used, other forms may be employed.

Figure 6:
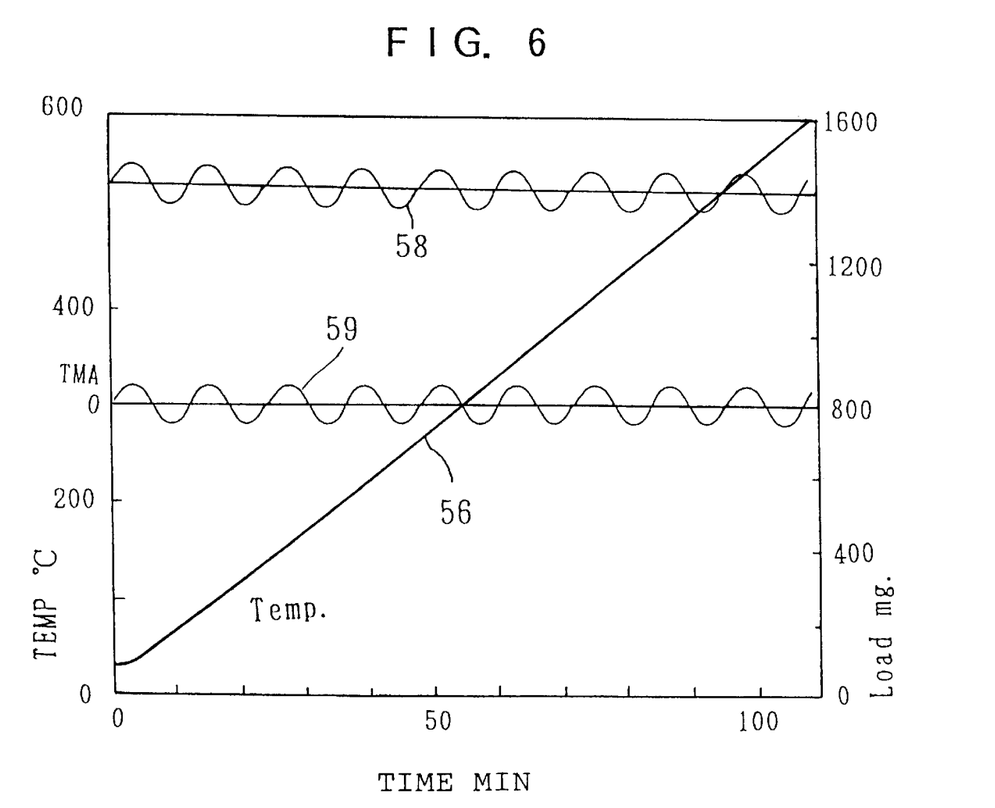
FIG. 6 is a graph showing results of TG measurement while vibrating a sample in specified sine waves by using the analyzer shown in FIG. 1.

The above-stated thermogravimetry is performed by keeping an output from the digital function generator 38 constant, particularly at zero, and without changing the position of the sample 1. Next, another method for measuring thermal weights will be described. The digital function generator 38 outputs a sine wave signal having a fixed angular frequency and a fixed amplitude. Other steps are the same as those described previously. The position of the sample 1 is moved in a sine wave form having a constant amplitude at a fixed angular frequency. In order to move the sample 1 in the specified sine wave form, a value based on a signal input to the load applying instrument 50 is supplied to the load register 43 and the storage instrument 34. The data thereof is shown in FIG. 6. Since the sine wave signal of a fixed angular frequency and a fixed amplitude has been supplied from the digital function generator 38, a signal is output to the load applying instrument 50 via the switch 42 in the D side so that the sample 1 may be vibrated in a specified sine wave of a fixed angular frequency and a fixed amplitude.

Since the sample 1 is vibrated in the sine wave of a fixed angular frequency and a fixed amplitude, the signal input to the load applying instrument 50 is, when detected, like that shown in FIG. 6. A line 58 in FIG. 6 indicates an external force produced by the load applying instrument 50 and applied to the sample 1. A line 59 indicates a displacement signal of the sample supporting means output from the differential transformer 5 at this time. Theoretically, in the line 59, an output from the digital function generator 38 and a profile are the same. At this time, a DC component to the load applying instrument 50 is a normal TG signal (weight change due to the temperature of the sample 1). A weight value obtained by dividing a ratio between the AC amplitude of a signal input to the load applying instrument 50 and the AC amplitude of a detected signal of the displacement detecting circuit 25 with a square of the angular frequency is a total weight between the sample supporting means and the number of vibrations of the sample 1. This makes it possible to calculate an inertial mass of the sample 1 in such a manner that with no sample placed in, a value obtained by dividing a ratio between the AC amplitude of the signal input to the load applying instrument 50 and that of the detected signal of the displacement detecting circuit 25 with a square of the angular frequency is calculated beforehand and this value is subtracted from the value when the sample is placed in. In this case, however, it is necessary to set a product obtained by squaring a displacement amplitude and the angular frequency to gravitational acceleration or lower so as to prevent the sample 1 from jumping.

Next, explanation will be made of TMA measurement in the analyzer of the invention by referring to FIGS. 1 and 2.

In FIG. 1, After the heating furnace 21 is lowered up to the limit by means of the moving mechanism 22 and the suspension type sample container 2 is removed, the tube-formed bellows 25 and the protective tube 13 used for TG measurement are removed by loosening the fixing nut 15. Further, the cap covering the opening part 26b in the cover 26 of the suspension type sample container 2 is removed, the connecting rod 6 is detached from the subfulcrum 7a of the arm 7 and the whole section composed of the connecting rod 6, the core 4 and the suspension wire 3 is pulled out upward.

Figure 2:
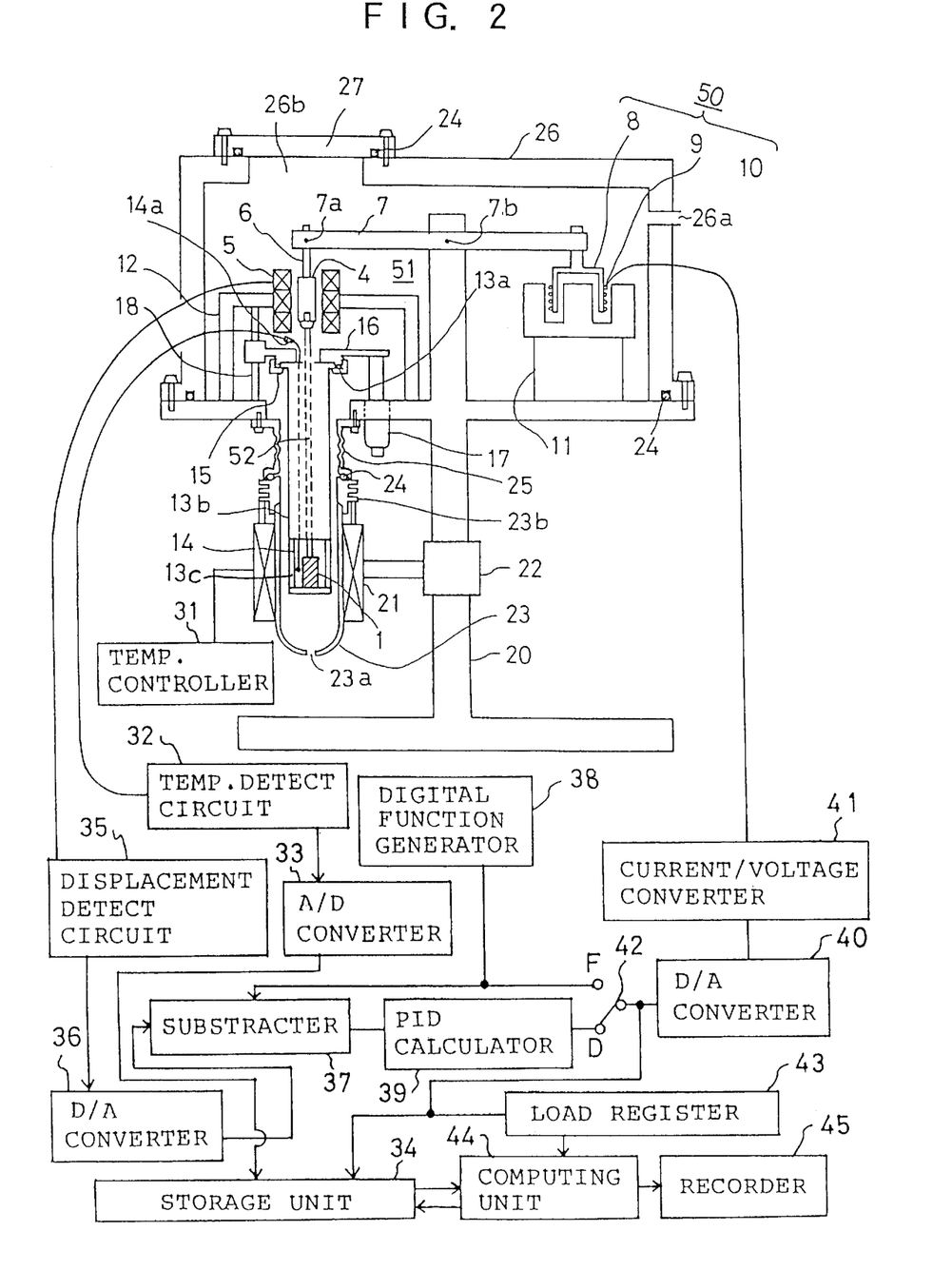
FIG. 2 is a sectional view showing in outline thermomechanical analysis (TMA) in the first embodiment.

Then, as shown in FIG. 2, instead of the protective tube 13 used for TG measurement, a tube-formed sample tube 13b having a bottom portion 13c and the thermocouple 14 fixed therein to the bottom portion 13c is attached to the sample holder 16 by the fixing nut 15. Further, the tube-formed bellows 25 is attached to the structuring member 20. The suspension wire 3 fixed by a screw shown in FIG. 1 is removed from the core 4, and instead, a detecting rod 52 is screw-fixed to the core 4 as shown in FIG. 2. The whole section composed of the connecting rod 6, the core 4 and the detecting rod 52 is interposed through the opening part 26b, the connecting rod 6 is placed so as to freely rotate around the subfulcrum 7a of the arm 7 and then the cap 27 is attached to the cover 26. In FIG. 2, the detecting rod 52, the core 4, the connecting rod 6 and the arm 7 constitute the sample supporting means. The sample supporting means functions to transmit an external force from the load applying instrument to the sample 1 and detect the deformation of the sample 1.

By setting the switch 42 to the F side (digital function generator 38 side), an output from the digital function generator 38 is set to a fixed value such that a load of a fixed downward direction, for instance 5 gf, can be applied to the second detecting rod 52. The sample tube 13b is lowered by means of the micrometer 17 according to the length of the sample 1 and the sample 1 is interposed between the bottom surface of the sample tube 51 and the detecting rod 52. After the position of the sample tube 51 has been adjusted by operating the micrometer 17 so as to make a displacement signal zero, the heating furnace 21 is raised to a specified position by means of the moving mechanism 22. When the temperature of the heating furnace 21 has been changed by the temperature controller 31 in accordance with a predetermined temperature program, the temperature of the sample 1 is captured by the thermocouple 14 and a change in the length of the sample in the longitudinal direction is detected as an output from the differential transformer 5. After having been digitized, these outputs are sent to the recording device 45 through the storage instrument 34 and the computing element 44 and output as TMA measurement data.

Figure 3:
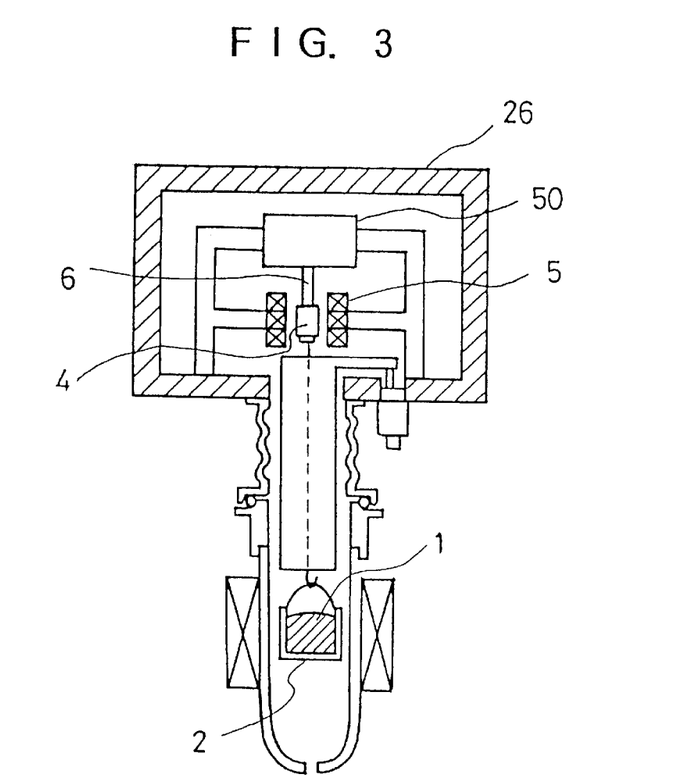
FIG. 3 is a sectional view showing main portions of another embodiment of the invention.
Figure 4:
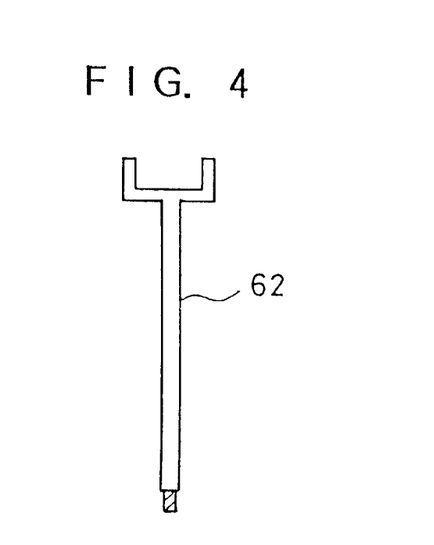
FIG. 4 is a partial sectional view showing yet another embodiment of the invention.

In the above-described embodiment, explanation was made of an example, in which as a temperature detector the thermocouple is used and the thermocouple 14 is placed differently from the suspension wire 3. Also, in the above-described embodiment, the balance composed of the arm 7 and its main fulcrum 7a is utilized for the detecting system and the displacement detector and the load applying instrument are placed in both ends of the balance. It is needless to say, however, that arrangement of the displacement detector and the load applying instrument is not limited to the example in the embodiment. Furthermore, the same effects can be obtained without using the balancing system, for instance by a structure shown in FIG. 3. In this structure, the load applying instrument 50 composed of the coil 9, the coil holder (not shown) and the magnet 10 is provided in the end opposite to the side of the detecting rod 6 to which the suspension wire 3 is attached. This does not have any balancing systems like that shown in the above-stated embodiment.

Furthermore, the analyzer may configured in a manner that the upper and lower portions are reversed in the two embodiments described above. In this case, the sample container 2 and the suspension wire 3 for TG measurement can be used by changing to an upper plate type sample container 62 with a container holding member as an integral part. Thus, common use of parts with the detecting rod 52 used for TMA measurement may be effected.

As apparent from the foregoing description, the invention allows easy and multifaceted analysis of the sample, reduction in spaces and costs and resource conservation, since both TMA measurement and macrotype TG measurement based on a gram order sample quantity can be performed by means of simple switching of the parts with one device. In particular, when the microtype TG device has already been provided, it is not necessary to newly prepare a machine specialized for macrotype TG, thereby preventing duplication of the devices.

This application relates to subject matter disclosed in Application number 7-175095, filed on Jul. 11, 1995 in Japan, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermal analyzer comprising:
    a heating furnace for heating a sample by a prescribed temperature program;
    a temperature detector placed in the vicinity of the sample for detecting a temperature of the sample;
    sample supporting means for supporting the sample;
    a displacement detector placed in a portion of the sample supporting means for detecting displacement of the sample supporting means;
    a load applying instrument for applying an external force to the sample via the sample supporting means;
    a control computing element for supplying to the load applying instrument a signal for controlling the external force applied from the load applying instrument to the sample so as to make the displacement of the sample supporting means zero based on an output signal from the displacement detector;
    a switch included in the control computing element for switching the control computing element to output to the load applying instrument a signal for controlling the external force applied from the load applying instrument to the sample to a predetermined value;
    processing circuitry for processing the signal supplied from the control computing element and the signal from the displacement detector to obtain thermogravimetry data and thermomechanical analysis data respectively, and
    a storage instrument responsive to the processing circuitry for storing the thermogravimetry data indicative of the signal supplied from the control computing element for controlling the external force applied from the load applying instrument to the sample so as to make the displacement of the sample supporting means zero at a first position of the switch and storing the thermomechanical analysis data indicative of the signal from the displacement detector at a second position of the switch.

2. A thermal analyzer according to claim 1, wherein the storage instrument is provided with a wind bag eliminating function for resetting a recorded value of an output from the load applying instrument to zero.

3. A thermal analyzer according to claim 1, further comprising:
    recording means for recording the thermogravimetry data stored by the storage instrument.

4. A thermal analyzer comprising:
    a heating furnace for heating a sample by a prescribed temperature program;
    a temperature detector placed in the vicinity of the sample for detecting a temperature of the sample;
    sample supporting means for supporting the sample;
    a displacement detector placed in a portion of the sample supporting means for detecting displacement of the sample supporting means;
    a load applying instrument for applying an external force to the sample via the sample supporting means;
    a control computing element for supplying to the load applying instrument a signal for controlling the external force applied from the load applying instrument to the sample so as to make the displacement of the sample supporting means a fixed value based on an output signal from the displacement detector;
    a switch included in the control computing element for switching the control computing element to output to the load applying instrument a signal for controlling the external force applied from the load applying instrument to the sample to a predetermined time function value;
    processing circuitry for processing the signal supplied from the control computing element and the signal from the displacement detector to obtain thermogravimetry data and thermomechanical analysis data, respectively, and
    a storage instrument responsive to the processing circuitry for storing the thermogravimetry data indicative of the signal from the control computing element for controlling the external force applied from the load applying instrument to the sample so as to set the displacement of the sample supporting means to the fixed value at a first position of the switch and storing the thermomechanical analysis data indicative of the signal from the displacement detector at a second position of the switch.

5. A thermal analyzer comprising:

a heating furnace for heating a sample by a prescribed temperature program;

a temperature detector placed in the vicinity of the sample for detecting a temperature of the sample;

sample supporting means for supporting the sample;

a displacement detector placed in a portion of the sample supporting means for detecting displacement of the sample supporting means;

a load applying instrument for applying an external force to the sample via the sample supporting means;

a control computing element for supplying to the load applying instrument a signal for controlling the external force applied from the load applying instrument to the sample so as to set the displacement of the sample supporting means to a predetermined sine, wave function or a function obtained by adding a fixed value to the predetermined sine wave function based on an output signal from the displacement detector;

a switch included in the control computing element for switching the control computing element to output to the load applying instrument a signal for controlling the external force applied from the load applying instrument to the sample to a predetermined value;

processing circuitry for processing the signal supplied from the control computing element and the signal from the displacement detector to obtain a value indicative of the signal supplied from the control computing element and a value indicative of the signal from the displacement detector respectively: and a storage instrument responsive to the processing circuitry for storing as a function of a temperature signal from the temperature detector the value indicative of the signal supplied from the control computing element for controlling the external force applied from the load applying instrument to the sample so as to set the displacement of the sample supporting means to the predetermined sine wave function or a function obtained by adding a fixed value to the predetermined sine wave function at a first position of the switch and storing as a function of a temperature signal from the temperature detector the value indicative of the signal from the displacement detector at a second position of the switch.

6. A thermal analyzer comprising:

a heating furnace for heating a sample;

a temperature detector placed in the vicinity of the sample for detecting a temperature of the sample;

a sample supporting device for supporting the sample;

a displacement detector adjacent to the sample supporting device for detecting displacement of the sample supporting device and providing a signal representative of the displacement;

a load applying instrument for applying an external force to the sample via the sample supporting means;

a control computing device for supplying to the load applying instrument a signal for controlling the external force to be applied from the load applying instrument to the sample so as to make the displacement of the sample supporting means zero based on the signal from the displacement detector;

a switch for allowing the control computing element to output to the load applying instrument one of a signal for controlling the external force applied from the load applying instrument to the sample and a predetermined value;

processing circuitry for processing the signal supplied from the control computing element and the signal from the displacement detector to obtain first data indicative of the signal supplied from the control computing element and second data indicative of the signal from the displacement detector, respectively: and a storage instrument responsive to the processing circuitry for storing the first data indicative of the signal supplied from the control computing element for controlling the external force applied from the load applying instrument to the sample so as to make the displacement of the sample supporting means zero at a first position of the switch and storing the second data indicative of the signal from the displacement detector at a second position of the switch.

7. A thermal analyzer according to claim 6, wherein the first data is thermogravimetry data and the second data is thermomechanical analysis data.

8. A thermal analyzer comprising:

a heating furnace for heating a sample;

a temperature detector placed in the vicinity of the sample for detecting a temperature of the sample;

sample supporting means for supporting the sample;

a displacement detector placed in a portion of the sample supporting means for detecting displacement of the sample supporting means;

a load applying instrument for applying an external force to the sample via the sample supporting means;

a control computing element for supplying to the load applying instrument a signal for controlling the external force applied from the load applying instrument to the sample so as to make the displacement of the sample supporting means a fixed value based on an output signal from the displacement detector;

a switch for allowing the control computing element to output to the load applying instrument one of a signal for controlling the external force applied from the load applying instrument to the sample and a predetermined time function value;

processing circuitry for processing the signal supplied from the control computing element and the signal from the displacement detector to obtain first data indicative of the signal supplied from the control computing element and second data indicative of the signal from the displacement detector, respectively; and a storage instrument responsive to the processing circuitry for storing the first data indicative of the signal from the control computing element for controlling the external force applied from the load applying instrument to the sample so as to set the displacement of the sample supporting means to the fixed value at a first position of the switch and storing the second data indicative of the signal from the displacement detector at a second position of the switch.

9. A thermal analyzer according to claim 8, wherein the first data is thermogravimetry data and the second data is thermomechanical analysis data.

10. A thermal analyzer comprising:

a heating furnace for heating a sample;

a temperature detector placed in the vicinity of the sample for detecting a temperature of the sample;

sample supporting means for supporting the sample;

a displacement detector placed in a portion of the sample supporting means for detecting displacement of the sample supporting means;

a load applying instrument for applying an external force to the sample via the sample supporting means;

a control computing element for supplying to the load applying instrument a first signal for controlling the external force applied from the load applying instrument to the sample so as to set the displacement of the sample supporting means to a predetermined sine wave function or a function obtained by adding a fixed value to the predetermined sine wave function based on an output signal from the displacement detector;

a switch for allowing the control computing element to output to the load applying instrument one of the first signal for controlling the external force applied from the load applying instrument to the sample and a predetermined value;

processing circuitry for processing the first signal supplied from the control computing element and the signal from the displacement detector to obtain a value indicative of the first signal supplied from the control computing element and a value indicative of the signal from the displacement detector, respectively; and a storage instrument responsive to the processing circuitry for storing the value indicative of the first signal supplied from the control computing element as a function of a temperature signal supplied from the temperature detector at a first position of the switch and storing the value indicative of the signal from the displacement detector as a function of a temperature signal from the temperature detector at a second position of the switch.

* * * * *